United States Patent [19]

Ruiz

[11] Patent Number: 4,464,780
[45] Date of Patent: Aug. 7, 1984

[54] PEDIATRIC RESTRAINT FOR X-RAY PHOTOGRAPHY

[76] Inventor: Gilbert G. Ruiz, 2614 N. Sterling Dr., McHenry, Ill. 60050

[21] Appl. No.: 409,439

[22] Filed: Aug. 19, 1982

[51] Int. Cl.³ .................................. A61B 6/04
[52] U.S. Cl. .................................. 378/178; 378/180
[58] Field of Search ................ 378/180, 208; 269/328

[56] References Cited

U.S. PATENT DOCUMENTS

| | | | |
|---|---|---|---|
| 2,780,730 | 2/1957 | Frohman et al. | 378/178 |
| 2,790,083 | 4/1957 | Snawder et al. | 378/178 |
| 2,926,256 | 2/1960 | Rankin | 378/178 |

Primary Examiner—Alfred E. Smith
Assistant Examiner—T. N. Grigsby
Attorney, Agent, or Firm—Howard H. Darbo

[57] ABSTRACT

Restraint apparatus is provided for immobilizing a pediatric patient during exposure of X-ray film, particularly in connection with chest examinations. The invention permits considerable reduction in the extent of exposure area of the patient's body. Manual restraint is not required and hence non-patient exposure to radiation is avoided. Because movement is restrained, the need to re-expose the patient is virtually eliminated. Adjustment is provided for the comfortable accommodation of infants up to small children. The apparatus secures both arms of an infant or small child in a forward and upward extension to achieve proper anatomical positioning for anterior-posterior or lateral chest X-ray study. Adjustable holders for different size film cassettes form part of the apparatus.

19 Claims, 4 Drawing Figures

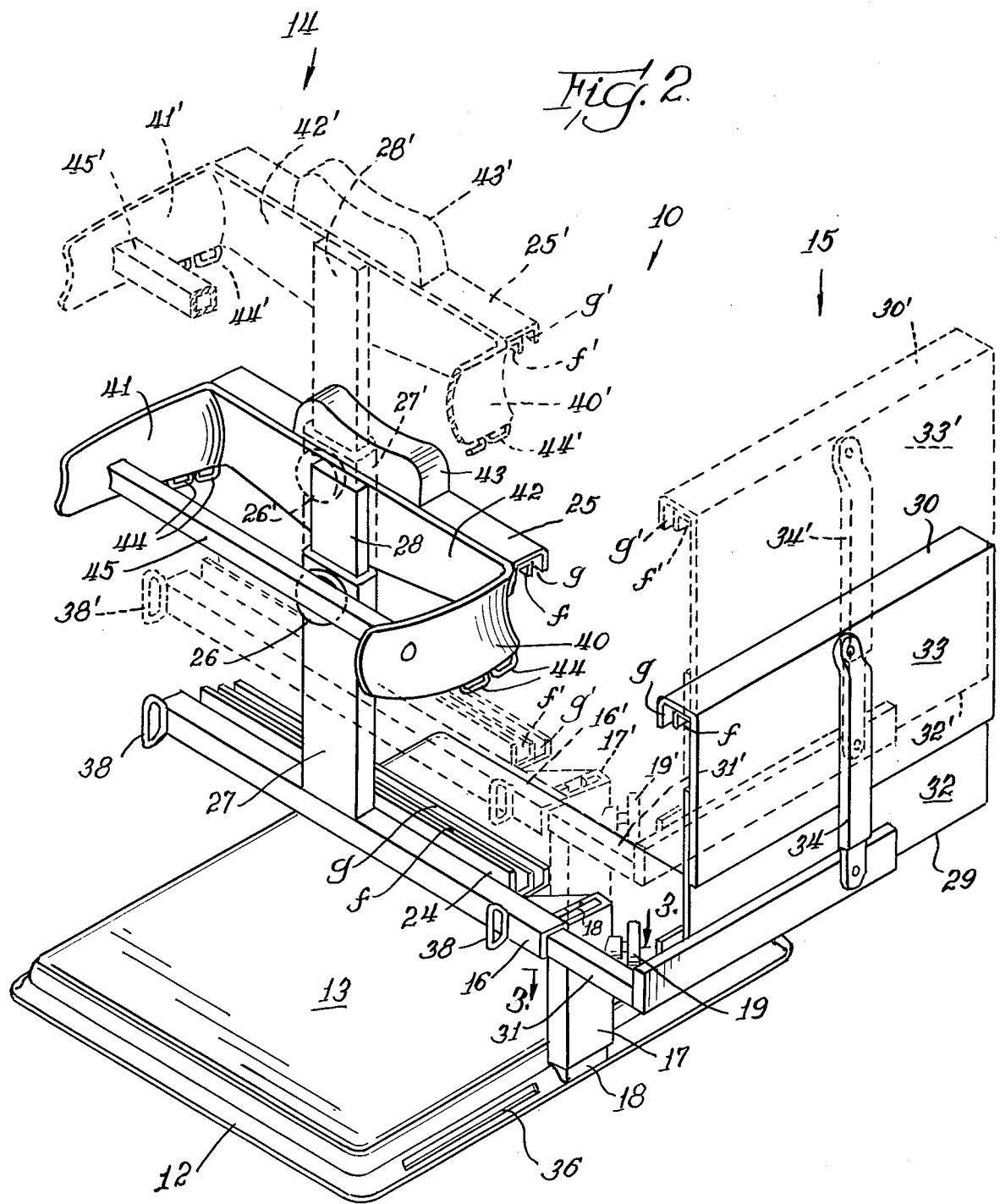

PEDIATRIC RESTRAINT FOR X-RAY PHOTOGRAPHY

BACKGROUND AND SUMMARY OF THE INVENTION

Chest examinations by X-ray photography commonly require exposure of X-ray film while an infant or child is in an upright position. The chest X-ray examination typically involves anterior-posterior and lateral exposures.

Because the cooperation of babies and small children in these X-ray procedures is often lacking, it is usually necessary that an adult manually restrain the child while the film is being exposed. Unfortunately, this subjects the adult to the risk of exposure to X-ray radiation. Even with this form of immobilization inadvertent movement can easily take place. If the patient is not motionless during exposure, clouding or double-imaging occurs necessitating retakes of the photograph to achieve a clear image.

Previous restraining devices have been provided for immobilizing young children during X-ray studies. U.S. Pat. Nos. 3,358,141, to Hoffmann et al., 3,526,222, to Dreibelbis, 3,650,523, to Darby, Jr., and, 3,933,154, to Cabansag, have offered immobilizers in the form of planar supports having straps for restraining the patient. The Cabansag patent further includes a flexible backer member allowing the patient to be placed in various orientations for X-ray examination of different parts of the anatomy.

U.S. Pat. No. 4,027,869, issued to this inventor, provides a planar member particularly suited for hip studies requiring the so-called frog-leg position.

These foregoing apparatuses do not include film holders and require that the apparatus, with restrained patient, be moved adjacent a film holding means. Further, such immobilizers require that they be radiotransparent in order to avoid shadows on the photographic images. Additionally, they must have sufficient sturdiness to permit moving the device and patient into proper anatomical positioning for the X-ray photograph.

U.S. Pat. Nos. 3,051,832, to Pigg, and 3,892,399, to Cabansag, disclose restraining apparatuses which include film holding means positioned adjacent the immobilization portions. The Pigg device restrains the child in a body-conforming structure which holds the child upright with arms extending vertically above the head. Straps or bands are not the primary restraining device but rather two opposing body-conforming portions are laterally expansible to accommodate various sized children therebetween. Held in such fashion, the patient may be rotated to the desired anatomical position in front of the X-ray film holder. The child's legs extend unrestrained below a mid-body planar section whereby undesired movement may take place. Also, with the arms held above the head, an uncomfortable position is imposed, which may lead to disquietude in the young patient.

The Cabansag apparatus is a chair-like device which positions the patient in a seated fashion with his back next to a film holder. The device further provides a lateral film holder, which may be pivotable. Like the Pigg structure, the Cabansag restraint may be rotatable. The film holding means is radially dislocatable to permit rotation of the chair-like device. A radio-transparent backer for the chair is needed inasmuch as it is disposed between the patient and film. The Cabansag apparatus offers restraints for the head, torso, legs and ankles. The examinee's arms may be restrained upwardly, above the shoulders, with a pair of arm straps at either side of a head restraining strap.

It is a primary goal of the invention to provide a simplified pediatric retraining device which affords comfortable positioning of the patient with minimal strapping to achieve the proper anatomical posture for anterior-posterior or lateral X-ray examination of the upper torso of the child.

It is an important object of the invention to provide an adjustable restraining apparatus for use with children up to about four years of age which affords adjustment of only a single vertical adjustment means to accommodate young patients in this range of sizes.

It is further an object of the invention to provide adjustable film holding means for X-ray film cassettes which can accommodate different sized film cassettes.

It is also an important goal of the invention to restrain the arms of the patient upwardly and outwardly on wing-like extensions forming arm rest means which attains the correct and preferred anatomical positioning of the chest for X-ray study.

It is an allied object of the invention to restrain the child with a minimum number of straps in a relatively comfortable position to gain patient cooperation and calmness.

It is therefore a concomitant object of the invention to position the patient in a seated position with arms restrained and supported in a relaxing posture at resting surfaces having an upward and outward extension.

It is also an object of the invention to provide a relatively inexpensive device which is portable, easily stored, and requires only minor adjustments for patient and film sizes.

It is an aim of the invention to securely immobilize the patient with a back strap, leg strap and arm straps by which the immature patient may be constrained in a relatively natural position.

It is a concomitant object of the invention to include means for holding grid filter panels which is formed integrally with the film cassette holding means.

The invention may be summarized as having a generally rectangular planar padded seat whereupon the patient sits lengthwise. At one end, the seat has overlying straps for leg restraint. An upright is fixed along a side edge of the seat with a vertically sliding sleeve engaged therearound. A locking knob means serves to vertically adjust the sleeve to desired positions. A cross framework associates with a side framework, and both are vertically movable by adjusting the sliding sleeve. The cross framework extends across the seat generally above the patient's thighs. The side framework extends along the side of the seat laterally of the patient's chest. Each framework includes film holding means having a pair of upper and lower, opposingly faced, horizontal double-channel members. Independent channel adjustment means are cooperative with each pair of double-channel members. The channel adjustment means movably interconnect the double-channel members and provide for relative vertical movement of the opposing double-channel members for the accommodation of different sized X-ray film cassettes.

The cross framework further includes wing-shaped arm rests extending patient-outwardly and upwardly generally from opposite ends of the upper double-channel. The arms and upper back of the patient are restrained by strap and strap holder means associated with the arm rests for securement from wrist-to-wrist with the strap extending around the upper back, or shoulders, of the patient. A strap and strap holder means associate with the lower double-channel for restraint around the lower back of the pediatric patient. The chest is immobilized closely adjacent the cross framework, and the side framework is positioned laterally of the patient.

In the preferred form, the side framework connects to a supporting tubular cross-bar of the cross framework by means of a slide arm movably positioned within the tubular cross-bar. Thereby, the side framework is also laterally movable with respect to the seat and patient, as well as being vertically adjustable by means of the locking knob and sliding sleeve.

BRIEF DESCRIPTION OF THE DRAWING

FIG. 2 is a perspective view looking generally from the opposite side of the pediatric restraint as shown in FIG. 1, depicting, in dashed lines, the adjustments of the cross and side frameworks and the film holding means.

DESCRIPTION OF MODE BEST EMBODYING THE INVENTION

Figure 1:
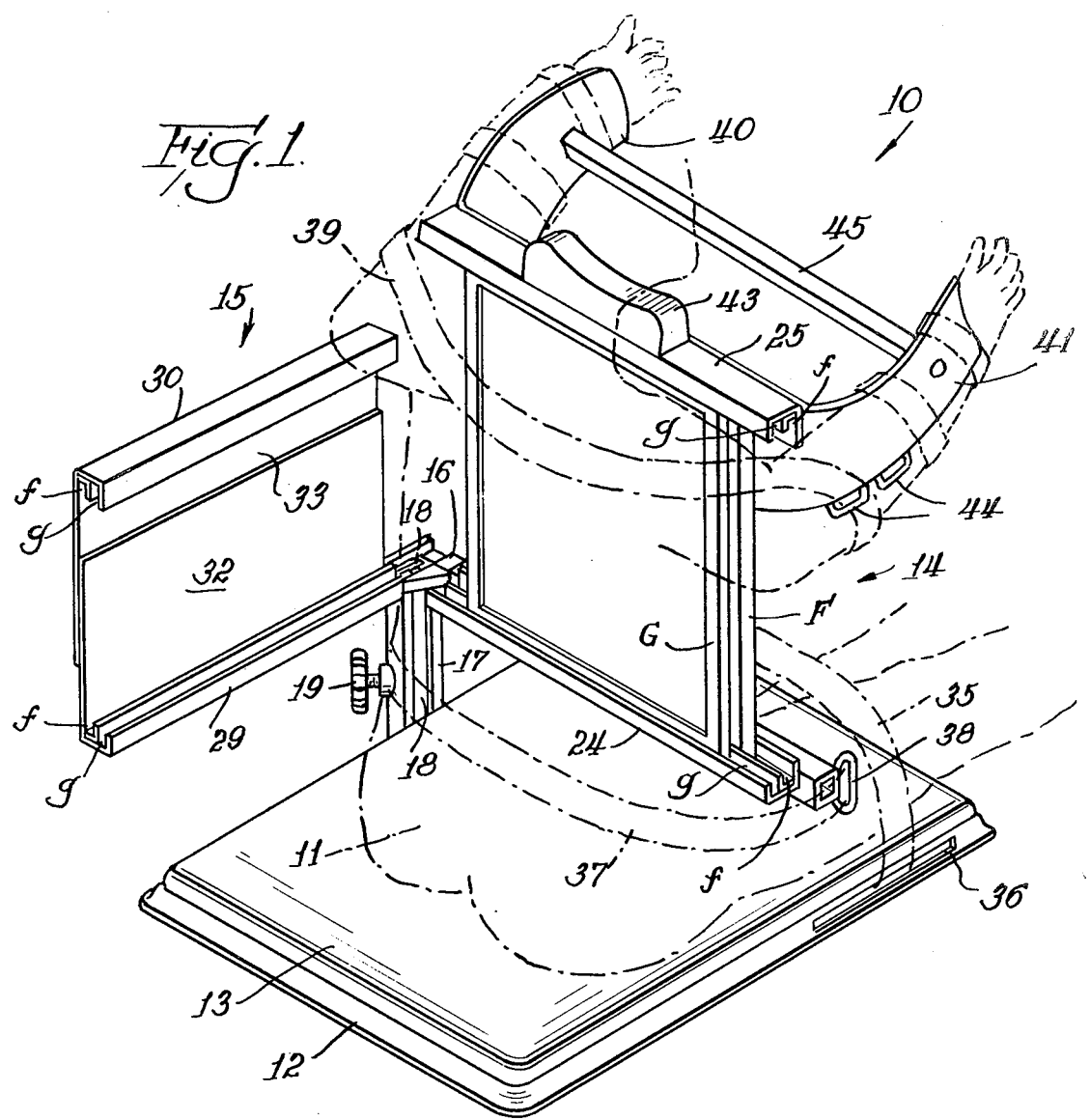
FIG. 1 is a perspective view of the pediatric restraint in accordance with the invention having an immobilized patient shown in phantom.
Figure 3:
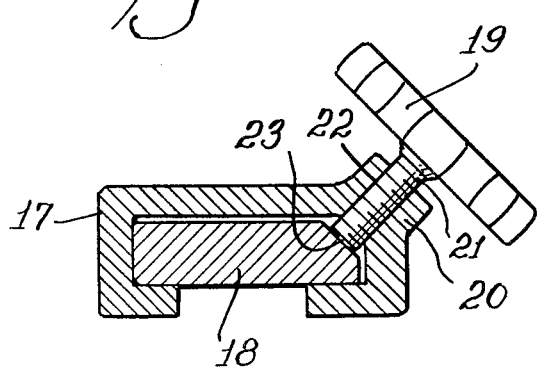
FIG. 3 is a cross-sectional view taken along line 3—3 of FIG. 2 showing the locking knob in association with the adjustable sliding sleeve and fixed upright member.

It will be seen from the Figures, that the invention embodied by pediatric restraint device 10, or pediatric restraint means, is intended for use with a small child or infant. An infant 11 is placed chest-forwardly adjacent a film cassette for the anterior-posterior X-ray photography position. A second film cassette may reside to the side of the infant for a lateral X-ray exposure.

The pediatric restraint means utilizes a limited number of restraining straps thus affording as much comfort as possible to the patient in reducing fear and nervousness which sometime attend examination of the immature patient.

The child is seated with legs extending forwardly chest closely adjacent a film cassette. His arms extend upwardly and outwardly, comfortably supported in wing-shaped arm rests, as will be described. Correct anatomical positioning of the child is attained with the relatively relaxed, but restrained, positioning of the child as shown.

In the illustrated embodiment, film holding adjustment is made possible for typical 8"×10" to 10"×12" size cassettes. Additionally, adjustment means is provided for the accommodation of smaller or larger children in the age group from infant up to about 3½ to 4 years of age.

With more specific reference to the Figures, it will be seen that child 11 sits lengthwise on top of a rectangular planar seat 12 over which a padded cushion 13 is affixed. The child is seated in an upright fashion with the torso generally at right angles to the planar seat 12 and his legs extended forwardly.

The patient's chest is positioned closely adjacent across framework 14 which includes means for positioning the arms and chin, as well as including means for holding a film cassette and filtering grid. X-ray filtering grids are used to eliminate scattered radiation and produce better film quality. Sideward of the child 11, a side framework 15 extends generally at right angles from cross framework 14. Side framework 15 has means for holding a laterally disposed film cassette and filtering grid.

Cross framework 14 includes a tubular cross-bar 16 which is fixed to a movable, or sliding, sleeve 17. The movable sleeve 17 has a generally block-C configuration with a central channel receiving an upright 18. Upright 18 is fixed to a side edge of seat 12. Therefore, vertical movement of cross framework 14 is afforded by an up or down sliding action by sleeve 17 extending around upright 18. Once the elevation of tubular cross-bar 16 is determined for positioning above the thighs of child 11, an adjustment lock knob 19 is tightened to maintain this height. The locking adjustment provision is afforded by a boss 20 integrally formed with sleeve 17 at a corner thereof and having a threaded slot 21 for thread engagement with threaded shaft 22 extending from knob 19. The upright 18 has a beveled corner 23 positionally aligned with the threaded slot 21 of the boss onto which the threaded shaft 22 is forced for locked positioning.

Cross framework 14 includes opposingly faced double-channel members 24, 25. The opposing pairs of channels are aligned for vertical placement of film cassette F and grid G. The patient-adjacent channels g-g receive the grid G and the channels f-f receive film cassette F, as shown in FIG. 1. Relative vertical spacing of members 24, 25 is attained by channel adjustment means comprising adjustment knob 26 in cooperation with vertical support channel 27 and movable bar 28. Support channel 27 is centrally fixed to tubular cross-bar 16 and extends upwardly to be slide engaged by movable bar 28. Double-channel 25 is affixed to movable bar 28. Adjustment knob 26 is of conventional design wherein a threaded shaft extends through a slot (not shown) in support channel 27 to contact movable bar 28 upon tightening. Untightening renders movable bar 28 free to move along support 27 for positioning at the desired separation distance between members 24, 25. Thus, different height grids and film cassettes may be accommodated.

Side framework 15 includes opposingly faced double-channel members 29, 30. The double-channel members are movably interconnected by a channel adjustment means, as will be explained. The opposing pairs of channels are aligned for vertical placement of a film cassette and grid. The patient-adjacent channels g-g receive a grid (not shown) and channels f-f receive a film cassette (not shown).

Side framework 15 is associated with cross framework 14 by means of double-channel 29 being affixed to a horizontal support rod 31, which is slidably disposed within tubular cross-bar 16 and vertically carried thereby upon vertical movement of sleeve 17. Support rod 31 may be horizontally translated within tubular cross-bar 16 to afford lateral adjustability of side framework 15.

Double-channel member 29 includes a vertical panel 32 extending upwardly from the remote outer wall of channel f. Double-channel member 30 includes a vertical panel 33 extending downwardly from the outer wall of its channel f in a slightly offset and overlapping orientation with panel 32. A well-known friction-type retainer forms channel adjustment means and connects panels 32, 33 in a vertically adjustable relationship. Double-channel 30 is thereby capable of being raised or lowered relative to double-channel 29 for accommodation of different height grids and film cassettes.

Upon seating child 11 to face cross framework 14, leg restraint is attained by the provision of leg straps 35 extending around the thighs of the child and passing through strap slots 36 formed in seat 12. The lower back of the patient is restrained by back strap 37 passing around the child to be secured at strap holders 38 which are located at the ends of tubular cross-bar 16.

Seated in this upright position, immobilization in the correct anatomical position is completed by securement of the shoulders and arms. In the embodiment shown, a single arm strap 39 secures the left arm, shoulders and right arm.

Particularly characterizing the invention is the provision of arm rests 40, 41 extending upwardly and outwardly from cross framework 14. In the embodiment shown, the arm rests 40, 41 are fixed to a gusset 42 which is attached to movable bar 28. Thus, the double-channel 25, arm rests 40, 41 and gusset 42 are carried as a unit by movable bar 28.

The wing-shaped arm rests 40, 41 are concave, and may be padded, to allow the arms of the patient to be comfortably nested. Restraint 10 secures the patient's arms in a forward and upward extension to attain a desirable anatomical position. For added comfort and positioning of the head, a soft chin rest 43 is centrally located atop channel 30. Thereby, the patient's thorax is positioned directly against grid G to reduce any chance magnification.

Arm rests 40, 41 include strap holders 44 for attachment of restraining strap 39. The strap 39 may be encircled about the arm rests, as shown, for full restraint of the arm from the wrist back to the shoulder. The strap 39 passes across the upper back, between the arm rests, to effect restraint from the left wrist, across the back, to the right wrist of the patient. Thus, clouding or double-imaging is virtually eliminated by this very effective upper body restraint.

A cross-brace 45 extends between arm rests 40, 41 for rigidity and arm stability.

In FIG. 2, the lowest vertical position of the frameworks 14, 15 and the smallest separation distance of each of their film holder means are shown in solid lines. The highest vertical position and the largest film holder means separation distance are shown in phantom lines having "prime" reference numerals. Frameworks 14, 15 move together relative to seat 12 by adjustment of knob 19 and sleeve 17. To accommodate different sized film cassettes, the film holding means of the frameworks are independently adjustable by adjustment of knob 26 for cross framework 14 and by adjustment of friction retainer 34 for side framework 15. Further, lateral movement of side framework 15 is attained by the slideaction of support rod 31 within tubular cross-bar 16. Therefore, four quick adjustments are made possible by pediatric restraint 10.

Standard film cassettes, and corresponding filter grids, are typically 10" or 12" high. Accordingly, the adjustable film holding means provides for separation between the opposing double-channel members from 10" at the smallest position to 12" at the largest (FIG. 2). It has been determined that the adjustment range for sleeve 17 of from about 2" to 3" is satisfactory for positioning tubular cross-bar 16 over the thighs of child 11 and placing the chest adjacent cross framework 14. The low setting places cross-bar 16 about 3" above cushion 13 and about 5" to 6" at the high setting. This variability allows X-ray study of infants and small children.

Figure 4:
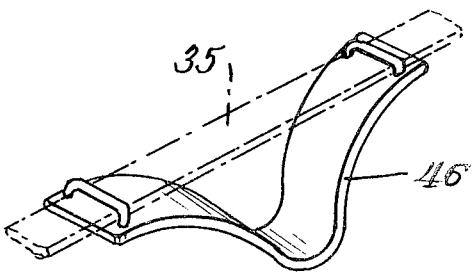
FIG. 4 shows an optional yoke-shaped leg restrainer for use with the leg strap of the pediatric restraint.

For additional restraint of the patient's legs, a yoke-shaped leg restrainer 47, as shown in FIG. 4, may be used in cooperation with leg strap 35 for disposition over the thighs.

While double-channel members are shown for the adjustable film holder means, it will be clear that single channels are within the scope of the invention when filter grids are not required. Of course, the double-channel members of restraint 10 are usable for film cassettes alone. The invention is not intended to be limited to the illustrated configurations of the elements embodying restraint 10, as will be clear to those skilled in X-ray examination technology.

ACHIEVEMENTS

Accordingly, the invention provides a comfortable, yet immobilizing, restraint for infants and small children. Wing-shaped arm rests have a concave formation for restful disposition of the patient's arms. A single strap preferably extends from one wrist across the patient's back to the other wrist for close positioning of the chest to a cross framework having film holder means. The lower back is secured by a strap extending from one side of the cross framework to restrain the patient in an upright seated position. Forward of the cross framework, the legs are secured to the seat for complete immobilization of the patient. A side framework, also including film holder means, associates with the cross framework and both frameworks are vertically adjustable by a single vertical adjustment means. The pediatric restraint is thereby adjustable for accommodation of infants up to small children. Anterior-posterior and lateral X-ray exposures may be made with certainty that clouding and double-imagery is virtually eliminated. Manual restraint is not needed and non-patient exposure to X-ray radiation is also eliminated.

Simple film holder adjustments allows different sized film cassettes and grids to be used.

The invention is lightweight and sturdy. With the child immobilized, the apparatus may be re-positioned relative to an X-ray machine in easy fashion.

The patient is secured in correct anatomical positioning at all times for chest X-ray examination. X-ray studies may quickly proceed with minimal discomfort and nervousness often encountered with the youthful patient.

What is claimed is:

1. A pediatric restraint suitable for immobilizing a child in an upright seated position for chest X-ray examination comprising:

a generally planar seat;

a cross framework extending across and over the planar seat, and including film holder means capable of holding X-ray film cassettes adjacent the chest of the seated patient;

vertically adjustable means at a side edge of the planar seat movably supporting said cross framework;

a side framework associated with the cross framework, being vertically carried thereby in response to said vertically adjustable means, and extending at right angles to said cross framework along said side edge of the planar seat, the side framework including film holder means capable of holding X-ray film cassettes laterally of the seated patient;

leg restraining means associated with said planar seat;

lower back restraining means associated with said cross framework;

arm and upper back restraining means associated with said cross framework including arm rest means extending upwardly and outwardly from said cross framework and being capable of supporting the patient's arms, whereby the patient can be restrained in an upright seated position with legs restrained beneath the cross framework and chest positioned closely adjacent the cross framework for anterior-posterior X-ray photography, and said side framework positioned sideward of the chest for lateral X-ray photography.

2. A pediatric restraint in accordance with claim 1 wherein the film holder means of said cross framework includes adjustment means whereby the film holder means is capable of holding different sized X-ray film cassettes.

3. A pediatric restraint in accordance with claim 2 wherein the film holder means of said cross framework comprises a pair of opposingly faced channel members, and said adjustment means movably interconnects the channel members and is capable of varying spacing therebetween.

4. A pediatric restraint in accordance with claim 3 wherein the channel members are horizontally disposed and said adjustment means is capable of varying vertical spacing therebetween.

5. A pediatric restraint in accordance with claim 1 wherein the film holder means of said side framework includes adjustment means whereby the film holder means is capable of holding different sized X-ray film cassettes.

6. A pediatric restraint in accordance with claim 5 wherein the film holder means of said side framework comprises a pair of opposingly faced channel members, and said adjustment means movably interconnects the channel members and is capable of varying spacing therebetween.

7. A pediatric restraint in accordance with claim 6 wherein the channel members are horizontally disposed and said adjustment means is capable of varying vertical spacing therebetween.

8. A pediatric restraint in accordance with claim 3 or 6 wherein the channel members are double-channeled forming a film cassette holding channel and a grid filter holding channel.

9. A pediatric restraint in accordance with claim 1 wherein the vertically adjustable means comprises a fixed upright member extending from said side edge of the seat, a vertically movable member movably engaged to the upright member, and means for locking the movable member at a predetermined height therealong.

10. A pediatric restraint in accordance with claim 9 wherein said cross framework includes a cross-bar extending across and above the seat and supportably associated with the vertically movable member facilitating vertical adjustment of said cross framework in response to said vertically adjustable means.

11. A pediatric restraint in accordance with claim 10 wherein said side framework is supportably associated with the cross-bar of said cross framework whereby said side framework moves in response to vertical adjustment of said cross framework.

12. A pediatric restraint in accordance with claim 11 wherein said cross-bar is tubular and said side framework includes a support bar connected at right angles thereto and being slidably disposed within said tubular cross-bar whereby said side framework is capable of independent lateral adjustment with respect to said seat by means of the slidable action of the support bar within the tubular cross-bar.

13. A pediatric restraint in accordance with claim 12 wherein the film holder means of said frameworks each comprises a pair of opposingly faced upper and lower channel members, the lower channel member of said cross framework supportably associated with said tubular cross-bar and the lower channel member of said side framework supportably associated with said slidable support bar.

14. A pediatric restraint in accordance with claim 1 wherein said arm rest means comprises two wing shaped members extending from opposite sides of said cross framework generally upwardly and outwardly with respect to said film holder means.

15. A pediatric restraint in accordance with claim 14 wherein said wing shaped members are concave.

16. A pediatric restraint in accordance with claim 1 wherein the restraining means for the legs, lower back, arms and upper back, include straps and strap holder means.

17. A pediatric restraint in accordance with claim 1 wherein the cross framework includes a chin rest for positioning the patient's throat adjacent to film holder means thereof.

18. In a pediatric restraint for immobilizing a small child in an upright seated position for chest X-ray examination, including film holding means, leg restraints and a generally planar seat, the improvement comprising:

cross framework means traversing the seat generally above the patient's thighs and having film holder means for disposing X-ray film closely adjacent the patient's chest, said cross framework including lower back restraining strap means and arm rest extensions projecting outwardly and upwardly for resting the patient's arms thereupon, and further including arm and upper back restraining strap means cooperative with said arm rests;

vertical adjustment means associating with said seat and movably connecting the cross framework means to the seat for adjustably positioning the cross framework at variable heights above said seat;

side framework means having means for connecting to said cross framework means generally at right angles thereto along a side of the seat laterally of the patient, said side framework means being movably adjustable in response to adjustment of said vertical adjustment means, and including film holder means for disposing X-ray film laterally of the patient's chest.

19. The improvement in accordance with claim 18 wherein at least one of the frameworks includes adjustable film holder means capable of accommodating different sized film cassettes.

* * * * *